United States Patent [19]

Gallagher et al.

[11] Patent Number: 5,430,067
[45] Date of Patent: Jul. 4, 1995

[54] PHARMACEUTICAL COMPOUNDS

[75] Inventors: Peter T. Gallagher, Camberley; Terence A. Hicks, Fleet; William M. Owton, Lightwater, all of England

[73] Assignee: Eli Lilly and Company, Indianapolis, Ind.

[21] Appl. No.: 289,076

[22] Filed: Aug. 11, 1994

[30] Foreign Application Priority Data

Aug. 13, 1993 [GB] United Kingdom ............... 9316923

[51] Int. Cl.$^6$ .............................................. A01N 37/10
[52] U.S. Cl. ...................................... 514/569; 552/262
[58] Field of Search ......................... 514/569; 552/262

[56] References Cited

U.S. PATENT DOCUMENTS 3,873,538  3/1975  Oxford et al. .................... 260/247.2
3,987,088  10/1976  Hodson et al. ...................... 260/475

FOREIGN PATENT DOCUMENTS 0570091  11/1993  European Pat. Off. .
WO92/10464  6/1992  WIPO ......................... C07D 69/96

OTHER PUBLICATIONS

Alexander et al., "Methylation and Hydroxylation Studies on Aloe–emodin," *J. Org. Chem.*, 45, 20–24 (1980).

Beilsteins Handbuch der Organischen Chemie, (4th ed., 3d Supp.), vol. 10, Part 5, pp. 4787–4790.

*Primary Examiner*—Paul J. Killos
*Attorney, Agent, or Firm*—James P. Leeds; David E. Boone; Gerald V. Dahling

[57] ABSTRACT

Pharmaceutical compounds as follows:
9,10-dihydro-9,10-dioxo-4,5,8-trimethoxyanthracene-2-carboxylic acid,
4,5-diethoxy-9,10-dihydro-9,10-dioxoanthracene-2-carboxylic acid,
9,10-dihydro-9,10-dioxo-4,5-dipropoxyanthracene-2-carboxylic acid,
4,5-dibutoxy-9,10-dihydro-9,10-dioxoanthracene-2-carboxylic acid,
9,10-dihydro-5,8-dimethoxy-9,10-dioxoanthracene-2-carboxylic acid,
7-acetoxy-9,10-dihydro-9,10-dioxoanthracene-2-carboxylic acid;

and salts and esters thereof.

3 Claims, No Drawings

PHARMACEUTICAL COMPOUNDS

This invention relates to pharmaceutical compounds.

The invention comprises certain 9,10-dihydro-9,10-dioxoanthracene-2-carboxylic acid compounds, which are useful in the treatment of connective tissue matrix diseases such as osteoarthritis, and in the treatment of cancer, said compounds being as follows:

9,10-dihydro-9,10-dioxo-4,5,8-trimethoxyanthracene-2-carboxylic acid, 4,5-diethoxy-9,10-dihydro-9,10-dioxoanthracene-2-carboxylic acid, 9,10-dihydro-9,10-dioxo-4,5-dipropoxyanthracene-2-carboxylic acid, 4,5-dibutoxy-9,10-dihydro-9,10-dioxoanthracene-2-carboxylic acid, 9,10-dihydro-5,8-dimethoxy-9,10-dioxoanthracene-2-carboxylic acid, 7-acetoxy-9,10-dihydro-9,10-dioxoanthracene-2-carboxylic acid;

and salts and esters thereof.

The compounds can exist in salt form derived from any of the well known bases. Preferably such salts are pharmaceutically-acceptable, but other salts are included as they may serve as intermediates in the purification of compounds or in the preparation of other salts, or are useful for identification, characterisation or purification. Examples are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

The compounds can also be utilised in ester form, esters being formed at the 2-carboxy group. These can be any of the well known ester groups, both aliphatic and aromatic. Preferred esters are those derived from an alcohol or an aminoalcohol, and particularly preferred are alkyl esters such as an ester of a $C_{1-4}$ alcohol, especially the methyl or ethyl ester.

As mentioned above, the compounds are indicated for use in the treatment of osteoarthritis and allied connective tissue diseases such as, for example, osteoporosis and rheumatoid arthritis. Such diseases are often characterised by an increase in matrix synthesis and remodelling. Incorporation of newly synthesised components into a biological and biomechanically functional matrix is, however, frequently deficient. Drugs which modulate the activity of the cells involved in such connective tissue matrix maintenance and repair are, therefore, of potential use in such diseases.

The compounds produce dose-dependent inhibition of in vitro tumour cell proliferation with IC50 values ranging from 1–50 $\mu$M. Partial inhibitory effects of around 30% were also observed for several compounds on tumour cell protein synthesis at a concentration of 100 $\mu$M using a method similar to that described by A. Floridi et al, Exp. Mol. Pathol., 1985, 42, 293–305. The majority of the compounds also inhibited mitogen-induced lymphocyte proliferation with IC50 values ranging from 10–100 $\mu$M.

Further modulatory effects of the compounds were observed in an in vitro model system used to study the differentiation of chondrocytes from prechondrogenic stem cells, as described by D. F. Paulsen et al, In Vitro Cellular and Developmental Biology 24, 138–147. The compounds demonstrate bimodal concentration effects on the production of matrix components by differentiating chick limb bud chondrocytes. Inhibitory effects of up to 95% were observed at concentrations ranging from 10–100 $\mu$M, whereas at submicromolar concentrations the compounds produced up to a three-fold stimulation in the synthesis of matrix macromolecules.

Further evidence of activity has been provided by studying the effect of compounds of the invention on lesions in guinea pigs. Spontaneous lesions of osteoarthritis were first described in the hind knee joints of old guinea pigs by Silverstein and Sokoloff (Arthritis Rheum. 1, 82–86 (1958)). Bendele and Hulman (Arthritis Rheum. 31, 561–565 (1988)) and Bendele, White and Hulman (Lab. Anim. Sci. 39, 115–121 (1989)) studied younger animals and were the first to describe the time course of progressing osteoarthritis in outbred male guinea pigs. These latter studies were confirmed and extended by Meacock, Bodmer and Billingham (J. Exp. Path. 71, 279–293 (1990)), also in outbred male guinea pigs.

The compounds of the invention are thus indicated for use in the treatment of osteoarthritis and allied connective tissue matrix diseases such as, for example, osteoporosis and rheumatoid arthritis. Furthermore, the inhibitory properties on tumour cell proliferation indicate that the compounds are of potential in the treatment of cancer.

The invention also includes a pharmaceutical composition comprising a pharmaceutically acceptable diluent or carrier in association with one or more of the above compounds or a pharmaceutically acceptable salt thereof.

The compounds can be prepared from known compounds by methods well known in the art. For example a useful starting point is rhein, or related analogues as disclosed in British Patent 1,578,452. Other compounds can be made by condensing appropriately substituted benzoic acid derivatives by the Friedel-Crafts reaction, followed by cyclisation, and subsequent demethylation or acetylation.

The compounds may be administered by various routes, for example by the oral or rectal route, topically or parenterally, for example by injection or infusion, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, ointments containing, for example, up to 10% by weight of the compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydrobenzoate, talc magnesium stearate and mineral oil. The compositions of the injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the conditions to be treated, the choice of compound to be administered and the chosen route of administration, and therefore the above dosage ranges are not intended to limit the scope of the invention in any way.

The invention is illustrated by the following Examples.

EXAMPLE 1

1,4,9-Trimethoxy-7-methylanthra-5,10-quinone

2-Methoxy-4-methylbenzoic acid diethyl amide (27 g) was dissolved in dry tetrahydrofuran (250 ml) with tetramethylethylenediamine (15 g). The solution was stirred under nitrogen and cooled to $-70°$ C. Tert-Butyl lithium (1.7N in pentane, 100 ml) was added over 15 minutes and the solution was stirred for 45 minutes. 2,5-Dimethoxybenzaldehyde (20 g) in dry tetrahydrofuran (80 ml) was added over 10 minutes. The reaction mixture was stirred for one hour at $-70°$ C. and then allowed to warm to room temperature. After 30 minutes water (10 ml) was added and the reaction mixture was concentrated down under reduced pressure. The resulting slurry was taken up in ethyl acetate (300 ml) and washed with 0.5N HCl (aq) (300 ml) and brine. The organic phase was dried (MgSO$_4$), filtered and concentrated to dry under reduced pressure. The resulting oil was dissolved in toluene, para-toluenesulfonic acid (1 g) was added and the solution was heated under reflux for 3 hours. The solution was allowed to cool, washed with 1N NaHCO$_3$ (aq), dried (MgSO$_4$) and filtered. The solution was evaporated to dryness under reduced pressure. The resulting solid was dissolved in ethyl acetate (250 ml) and hexane was added (150 ml). The solution was allowed to stand over night at $-20°$ C. The resulting precipitate was collected by filtration and dried to give 4-methyl-7-methoxy-3-(2′,5′-dimethoxyphenyl)-1-(3H)-isobenzofuranone, m.p. 121°–123° C.

4-Methyl-7-methoxy-3-(2′,5′-dimethoxyphenyl)-1-(3H)-isobenzofuranone (17 g) and triethylsilane (15 g) were dissolved in dichloromethane (200 ml) and stirred at room temperature under nitrogen. Titanium tetrachloride (5N in CCl$_4$, 25 ml) was added by syringe. The reaction mixture was stirred at room temperature for 4 hours. Water (10 ml) was added dropwise and the reaction mixture was concentrated down. The resulting slurry was dissolved (with heating) in 2N NaOH (aq) and filtered through celite. The filtrate was washed with diethyl ether (2×200 ml) and acidified with concentrated HCl (aq). The resulting precipitate was collected by filtration and dried to give 4-methyl-6-methoxy-2-(2′,5′-dimethoxybenzyl)benzoic acid, m.p. 172°–174° C.

4-Methyl-6-methoxy-2-(2′,5′-dimethoxybenzyl)benzoic acid (25 g) and polyphosphoric acid (200 g) was stirred with an overhead stirrer and heated to 85° C. for 30 minutes. The reaction mixture was allowed to cool and then water (400 ml) was added. The resulting yellow/green solid was collected by filtration to give 1,4,9 trimethoxy-7-methylanthracen-10-one, m.p. 177°–179° C.

1,4,9-Trimethoxy-7-methylanthracen-10-one (5 g) was dissolved in warm acetic acid (15 ml). Potassium dichromate (5 g) was dissolved in acetic acid (20 ml) at reflux. The anthracenone solution was added to the dichromate solution and the reaction mixture was heated under reflux for 20 minutes. The reaction mixture was allowed to cool and water (200 ml) was added. The yellow precipitate was collected by filtration and dried to give 1,4,9 trimethoxy-7-methylanthra-5,10-quinone, m.p. 189°–191° C.

9,10-Dihydro-9,10-dioxo-4,5,8-trimethoxyanthracene-2-carboxylic acid

To a solution of potassium permanganate (6.46 g) in deionised water (62 ml) was added dropwise at room temperature, with stirring, a solution of tetrabutyl ammonium bromide (13.9 g) in deionised water (25 ml). The deep purple suspension was stirred for one hour, filtered, washed with water and pulled dry. The purple solid was dissolved in pyridine (200 ml) and added dropwise over one hour to a solution of the methylanthraquinone (4.0 g) in pyridine (80 ml) under nitrogen at 75° C. with stirring. After addition, the reaction was stirred for a further hour, allowed to cool to 15° C. and sodium metabisulphite was added and the mixture allowed to stir over night at room temperature. Pyridine was evaporated off under reduced pressure, the residue dissolved in deionised water (300 ml), acidified with concentrated hydrochloric acid and cooled to 2° C. for 3 hours, filtered and pulled dry to leave a dark orange solid. Dried at 60° C. under vacuum to give 9,10-dihydro-9,10-dioxo-4,5,8-trimethoxyanthracene-2-carboxylic acid, m.p. 260°–262° C.

EXAMPLE 2

4,5-Diethoxy-9,10-dihydro-9,10-dioxoanthracene-2-carboxylic acid, ethyl ester

A mixture of 9,10-dihydro-4,5-dihydroxy-9,10-dioxoanthracene-2-carboxylic acid (2.84 g), anhydrous potassium carbonate (20.7 g) and diethylsulphate (9.64 g) was mechanically stirred in 'drierite' dried acetone (135 ml) and dioxan (120 ml) for 20.75 hours under reflux.

The mixture was filtered hot through Celite and the contents of the filter were washed with hot dioxan (2×50 ml).

The filtrate and washings were combined, then evaporated in vacuo. The residue was stirred in 40°–60° C. petroleum ether (50 ml), filtered and the resulting cream coloured solid was washed with 40°–60° C. petrol (3×50 ml).

After drying at 75° C. in vacuo the required triethylated compound was obtained, m.p. 140°–142° C.

The corresponding 4,5-dipropoxy and 4,5-dibutoxy compounds can be prepared by alkylation using the appropriate iodide.

4,5-Diethoxy-9,10-dihydro-9,10-dioxoanthracene-2-carboxylic acid 4,5-Diethoxy-9,10-dihydro-9,10-dioxoanthracene-2-carboxylic acid, ethyl ester (2.67 g) and crushed potassium hydroxide (1.22 g) were dissolved by magnetically stirring in water (13 ml) and dioxan (26 ml). Within 15 minutes a mustard coloured solid began to separate.

The suspension was stirred for a further 22 hours at room temperature before evaporating to dryness. The residue was dissolved in water (50 ml), then concentrated hydrochloric acid was added to adjust to pH1.

The resulting mustard coloured precipitate was removed by filtration and washed with water (3×25 ml), then acetone (25 ml).

After drying at 73° C. in vacuo the required diethoxy acid was obtained, m.p. 246°–247.5° C.

The corresponding 4,5-dipropoxy and 4,5-dibutoxy compounds can be prepared by a similar method.

EXAMPLE 3

9,10-Dihydro-5,8-dihydroxy-9,10-dioxoanthracene-2-carboxylic acid

Anhydrous aluminium chloride (75 g) and freshly dried (at ~310° C.) sodium chloride (15 g) were heated in a oil-bath, with mechanical stirring, to give a melt. The temperature of the melt was increased to 160° C., when addition of a finely ground intimate mixture of 1,2,4-benzene tricarboxylic anhydride (10.8 g) and hydroquinone (4.425 g), in a portionwise manner, was begun. Addition took 43 minutes, during which time the temperature had risen to 170° C. The now deep crimson-coloured reaction mixture was stirred for a further 1 hour at 165°–170° C. The bulk of the molten mass was poured into ice/water (500 ml). The aqueous solution was then used to wash out the reaction flask.

Concentrated HCl (50 ml) was added and the mixture heated on a steam bath for ~16 minutes. The resulting rust-coloured suspension was cooled in an ice-bath for 10 minutes, then filtered. The reddish-brown solid on the filter was washed with water (3×500 ml), then dried at 60° C. in vacuo. (2.5 g) of the product was soxhlet extracted with dioxan (250 ml) for 20 hours, stirred at room temperature for 5 hours and filtered to remove the reddish-brown solid which was washed on the filter with 40°–60° C. petrol (total 200 ml) and dried at 70° C. in vacuo.

9,10-Dihydro-5,8-dimethoxy-9,10-dioxoanthracene-2-carboxylic acid, methyl ester

A mixture of 9,10-dihydro-5,8-dihydroxy-9,10-dioxoanthracene-2-carboxylic acid (23 g), anhydrous potassium carbonate (166 g) and dimethyl sulphate (63.9 g) in acetone (2.5 L) and dioxan (2 L) was mechanically stirred and heated under reflux for 44.3 hours.

The reaction mixture was then filtered hot and the contents of the filter were washed with hot dioxan (4×250 ml). The combined filtrate and washings were evaporated at 62° C. in vacuo to remove the bulk of the solvents.

The residue was diluted with 40°–60° C. petroleum ether (1.25 L). The resulting suspension was filtered to remove the rust coloured solid product. After washing with 40°–60° C. petrol (0.5 L), then drying at 72° C. in vacuo, the required product was obtained, m.p. 214°–216° C.

9,10-Dihydro-5,8-dimethoxy-9,10-dioxoanthracene-2-carboxylic acid 9,10-Dihydro-5,8-dimethoxy-9,10-dioxoanthracene-2-carboxylic acid, methyl ester (0.8 g) and powdered potassium hydroxide (0.42 g) were magnetically stirred in water (4.3 ml), methanol (8.6 ml) and dimethyl sulphoxide (4.3 ml) for 22.25 hours at room temperature.

The resulting suspension was concentrated to remove the methanol, then water (16 ml) was added to effect dissolution.

0.5N hydrochloric acid was then added to adjust the solution to pH1.

The resulting reddish brown coloured precipiate was removed by filtration, then washed with water (150 ml).

After drying on a porous tile the solid had a melting point of 298°–299° C.

EXAMPLE 4

9,10-Dihydro-9,10-dioxo-7-hydroxyanthracene-2-carboxylic acid

A mixture of 9,10-dihydro-9,10-dioxo-7-fluoroanthracene-2-carboxylic acid (34.77 g) (prepared in accordance with Allen and Hanbury patent GB1339008 (1970)), sodium hydroxide pellets (25.73 g) and tetra n-butylammonium bromide (6.12 g) in water (522 ml) and chlorobenzene (1.2 L) was mechanically stirred under reflux for 23.5 hours.

After allowing the reaction mixture to cool, water (1.39 L) was added and, after stirring, two layers were allowed to separate.

The lower chlorobenzene layer was removed and extracted with water (350 ml).

The aqueous solutions were combined and adjusted to pH1 by addition of concentrated hydrochloric acid. The resulting mustard coloured suspension was filtered and the solid thus obtained was washed on the filter with water (1 L).

After drying at 70° C. in vacuo the required hydroxy compound was obtained, m.p. >320° C.

7-Acetoxy-9,10-dihydro-9,10-dioxoanthracene-2-carboxylic acid 9,10-Dihydro-9,10-dioxo-7-hydroxyanthracene-2-carboxylic acid (36.39 g) was suspended in glacial acetic anhydride (364 ml). Concentrated sulphuric acid (5 ml) was added and the mixture was stirred magnetically at 110°±5° C. for 6 hours in a heating mantle.

The resulting brown solution was allowed to stand at room temperature for 17 hours, during which time a light brown solid separated. After filtration, the solid was washed with water (200 ml), then ethyl acetate (200 ml), followed by stirring in 40°–60° C. petroleum ether (400 ml) for 15 minutes.

The acetylated product was removed by filtration, washed with 40°–60° C. petroleum ether (2×200 ml) and dried at 73° C. in vacuo, m.p. >320° C.

The following formulations of active compounds of the invention can be prepared.

EXAMPLE 5

Studies were carried out on exposure of guinea pigs following oral dosing of compounds of the invention. Each compound was dosed orally at 25 mg/kg body weight in suspension in carboxymethylcellulose. Plasma concentrations of compound or its hydrolysed product were measured over 0–8 hours. The area under the plasma concentration-time curve was calculated over this period and used to compare systemic exposure of the guinea pig with that of diacetyl rhein, a prior art compound.

The following compounds:
9,10-dihydro-9,10-dioxo-4,5,8-trimethoxyanthracene-2-carboxylic acid,
4,5-diethoxy-9,10-dihydro-9,10-dioxoanthracene-2-carboxylic acid,
9,10-dihydro-5,8-dimethoxy-9,10-dioxoanthracene-2-carboxylic acid,
were markedly superior to diacetyl rhein, which is an indication of their potentially superior bioavailability.

EXAMPLE 6

Soft Gelatin Capsule

Each soft gelatin capsule contains:

| Active ingredient | 150 mg |
|---|---|
| Arachis oil | 150 mg |

After mixing together, the blend is filled into soft gelatin capsules using the appropriate equipment.

EXAMPLE 7

Hard Gelatin Capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 8

Tablets each containing 10 mg of active ingredient are made up as follows:

| Active ingredient | 10 mg |
|---|---|
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

We claim:
1. A 9,10-dihydro-9,10-dioxoanthracene-2-carboxlic acid, selected from the group consisting of:
9,10-dihydro-9,10-dioxo-4,5,8-trimethoxyanthracene-2-carboxylic acid,
4,5-diethoxy-9,10-dihydro-9,10-dioxoanthracene-2-carboxylic acid,
9,10-dihydro-9,10-dioxo-4,5-dipropoxyanthracene-2-carboxylic acid,
4,5-dibutoxy-9,10-dihydro-9,10-dioxoanthracene-2-carboxylic acid,
9,10-dihydro-5,8-dimethoxy-9,10-dioxoanthracene-2-carboxylic acid,
7-acetoxy-9,10-dihydro-9,10-dioxoanthracene-2-carboxylic acid;
and salts and esters thereof.

2. A pharmaceutical formulation comprising a compound as defined in claim 1, or pharmaceutically-acceptable salt or ester thereof, together with a pharmaceutically-acceptable diluent or carrier therefor.

3. A method of treating an animal, including a human, suffering from or susceptible to a connective tissue matrix disease, or cancer, which comprises administering an effective amount of a compound as defined in claim 1, or a pharmaceutically acceptable salt or ester thereof.

* * * * *

UNITED STATES PATENT AND TRADEMARK OFFICE
CERTIFICATE OF CORRECTION

PATENT NO.    : 5,430,067

DATED         : July 4, 1995

INVENTOR(S)   : Peter T. Gallager, Terence A. Hicks, William M. Owton

It is certified that an error appears in the above-identified patent and that said Letters Patent is hereby corrected as shown below:

Column 8, claim 1, line 19, "2-carboxlic" should read, -- 2-carboxylic --.

Signed and Sealed this

Fourteenth Day of November, 1995

*Attest:*

BRUCE LEHMAN

*Attesting Officer*    *Commissioner of Patents and Trademarks*